(12) United States Patent
Cinelli et al.

(10) Patent No.: US 6,177,482 B1
(45) Date of Patent: *Jan. 23, 2001

(54) ADHESIVE FOR SECURE TOPICAL ATTACHMENT TO THE SKIN AND COMFORTABLE REMOVAL

(75) Inventors: Fabio Cinelli, Bologna; Peter Coles; Italo Corzani, both of Chieti, all of (IT)

(73) Assignee: The Proctor & Gamble Company, Cincinnati, OH (US)

( * ) Notice: Under 35 U.S.C. 154(b), the term of this patent shall be extended for 0 days.

This patent is subject to a terminal disclaimer.

(21) Appl. No.: 09/331,685

(22) PCT Filed: Dec. 22, 1997

(86) PCT No.: PCT/US97/23474

§ 371 Date: Jun. 23, 1995

§ 102(e) Date: Jun. 23, 1995

(87) PCT Pub. No.: WO98/28021

PCT Pub. Date: Jul. 2, 1998

(30) Foreign Application Priority Data

Dec. 23, 1996 (EP) .................................. 96120738
Jul. 1, 1997 (EP) .................................. 97110730
Nov. 20, 1997 (EP) .................................. 97120336

(51) Int. Cl.$^7$ ........................................ C08L 15/00
(52) U.S. Cl. .................. 523/111; 428/355 R; 523/105
(58) Field of Search .......................... 524/270, 277, 524/322, 481, 505, 578; 525/95; 523/105, 111; 428/343, 355 R, 354

(56) References Cited

U.S. PATENT DOCUMENTS

| | | | |
|---|---|---|---|
| 4,593,053 | * | 6/1986 | Jevne et al. ............................ 523/111 |
| 4,699,146 | * | 10/1987 | Sieverding ............................ 128/640 |
| 5,071,704 | | 12/1991 | Fischel-Ghodsian ................ 428/354 |
| 5,418,052 | * | 5/1995 | Sugie et al. ............................ 428/261 |
| 5,445,627 | | 8/1995 | Mizutani et al. ................. 604/385.2 |
| 5,559,165 | * | 9/1996 | Paul ....................................... 523/111 |
| 5,658,270 | | 8/1997 | Lichstein ............................... 604/387 |

FOREIGN PATENT DOCUMENTS

| | | | |
|---|---|---|---|
| 643 730 | 6/1984 | (CH) | ............................... A61F/13/16 |
| 1 934 710 | 1/1970 | (DE) | . |
| 0 184 470 | 6/1986 | (EP) | ............................... A61L/15/06 |
| 0 611 575 A1 | 2/1994 | (EP) | ............................... A61L/15/58 |
| 2 734 574 | 11/1996 | (FR) | ............................... C09J/133/02 |
| 2 115 431 | 9/1983 | (GB) | ............................... C09J/3/14 |
| 55-092306 | 7/1980 | (JP) | ............................... A61K/7/00 |
| 62-209008 | 9/1987 | (JP) | ............................... A61K/7/00 |
| WO 93/10201 | 5/1993 | (WO) | ........................... C09J/139/04 |
| 16424 | * 6/1995 | (WO) | ........................................ 13/58 |
| WO 95/16424 | 6/1995 | (WO) | ............................ A61F/13/58 |
| WO 96/13238 | 5/1996 | (WO) | ............................ A61F/13/56 |
| WO 96/14822 | 5/1996 | (WO) | ............................ A61K/7/00 |

* cited by examiner

Primary Examiner—Edward J. Cain
Assistant Examiner—Katarzyna Wyrozebski
(74) Attorney, Agent, or Firm—Leonard W. Lewis; Jerry Yetter; Mathew P. Fitzpatrick

(57) ABSTRACT

The present invention relates to topical adhesives for attachment to the skin. In particular the present invention relates to such topical adhesives which can be employed for attachment to the skin of articles such as protective articles, clothing, prosthesis, heat wraps, pads, and/or packs, e.g. for topical relief of pain or simply to provide warmth, cold wraps hearing aids, protective face masks, ornamental articles or eye wear, but excluding absorbent articles, or also of functional articles such as cosmetic or pharmaceutical delivery articles that provide a substance to the skin, decorative cosmetics or cleaning articles. The topical adhesive provides secure attachment and is pleasing to the skin upon application, yet causes no discomfort upon removal. This is achieved by selecting the characteristics of the topical adhesives, particularly the viscous modulus G" in combination with the thickness C of the topical adhesive layer in which the adhesive is provided for attachment to the skin.

9 Claims, No Drawings

ADHESIVE FOR SECURE TOPICAL ATTACHMENT TO THE SKIN AND COMFORTABLE REMOVAL

FIELD OF THE INVENTION

The present invention relates to topical adhesives for attachment to the skin, said adhesive being provided as a layer. In particular the present invention relates to such topical adhesives which can be employed for attachment to the skin, particularly for the adhesion of protective articles such as genital-, knee- or elbow-protectors or bandages; clothing such as bras, surgical gowns, or parts of garments during fitting at a tailor; nasal plasters; prosthesis such as breast replacements or wigs; heat wraps, pads, and/or packs, e.g. for topical relief of pain or simply to provide warmth; cold wraps e.g. to provide pain relieve from bruises and to reduce swelling; hearing aids; protective face masks; ornamental articles such as jewelry, earrings, guises, tattoos; goggles or other eye wear. Further, the topical adhesive can be employed for application of functional articles to the skin, particularly for the adhesion of functional articles or the improvement of the function of such articles. Functional articles in this context are cosmetic or pharmaceutical delivery articles which provide a substance to the skin such as skin treatment substances, creams, lotions, hormones, vitamins, deodorants, or drugs; alternatively cosmetic or pharmaceutical delivery articles can also provide a substance to emanate away from the skin such as insecticides, inhalation drugs, or perfumes; the adhesive of the present invention can also be used in functional articles which are not attached to the skin but as a component in articles which require a high residence time on the skin such as decorative cosmetics (lipstick, eye colors, stage make-up) or cleaning article (hand cleaner, face mask, hygienic cleanser especially for pores). The topical adhesive provides secure attachment or increased residence time and is pleasing to the skin upon application, yet causes no discomfort upon removal. This is achieved by selecting the characteristics of the topical adhesives, particularly the viscous modulus G" of the topical adhesive and the thickness C of the layer of topical adhesive applied to the article.

BACKGROUND OF THE INVENTION

The general prior art in the field of topical adhesives for attachment to the skin is particularly developed in the field of band-aids, plasters and bandages. These articles are, however, typically applied in an emergency situation where for example a cut into the skin of the wearer has occurred and absorption of the body liquids emanating from a wound is desired. In this context performance aspects of the absorbent article such as comfortable and easy use and application, painless removal, discreteness are subordinate to criteria such as sterility, healing support, mechanical protection of the wound. Also such wound covering absorbent articles are mostly adhered to skin areas where prior to application of the absorbent article body hair can be removed or where little or no hair grows.

The present invention relates to topical adhesives which are particularly useful to protective articles such as genital-, knee- or elbow-protectors or bandages; clothing such as bras, surgical gowns, or parts of garments during fitting at a tailor; nasal plasters; prosthesis such as breast replacements or wigs; heat wraps, pads, and/or packs, e.g. for topical relief of pain or simply to provide warmth; cold wraps e.g. to provide pain relieve from bruises and to reduce swelling; hearing aids; protective face masks; ornamental articles such as jewelry, earrings, guises, tattoos; goggles or other eye wear. Such articles are not used for absorption of body liquids. For example attachment of a wig to the skin on the skull or of elbow and knee protectors to these surfaces of the body which undergo substantial extending and wrinkling can suitably be done by the adhesive of the present invention.

The present invention can further relate to topical adhesives which are particularly useful to functional articles such as cosmetic or pharmaceutical delivery articles which provide a substance to the skin such as skin treatment substances, creams, lotions, hormones, vitamins, deodorants, or drugs; alternatively cosmetic or pharmaceutical delivery articles can also provide a substance to emanate away from the skin such as insecticides, inhalation drugs, or perfumes; further the adhesive of the present invention can also be used in functional articles which are not attached to the skin but as a component in articles which require a high residence time on the skin such as decorative cosmetics (lipstick, eye colors, stage make-up) or cleaning article (hand cleaner, face mask, hygienic cleanser especially for pores). Such articles are not used for absorption of body liquids. For example attachment of a vitamin plaster to the skin or of an inhalation drug releasing article to the breast can suitably be done by the adhesive of the present invention. Inclusion of the adhesive into decorative cosmetics allows to increase their resistance to wearing off while not creating a removal problem.

Topical adhesives that are used for absorbent articles such as sanitary napkin and pantiliners have generally been disclosed in US statutory invention registration H1602 or WO 96/33683. Some more details of the adhesive have been disclosed in PCT application WO 95/16424. In this document sanitary articles having a topical adhesive which is applied on the wearer facing side of a sanitary napkin along the entire periphery are disclosed. The problem underlying this document is primarily the safe attachment to the skin but mentions also the problems of detachment of such articles after use without causing undue pain to a wearer.

The disclosure of WO 95/16424 includes a detailed analysis of the criteria for the topical adhesive in respect to rheological criteria. However, this document has little regard to the problem of painless removal of such articles since the rheological criteria taught include epilatory, i.e. hair removal, compositions which are commercially available such as STREP MIELE (TM) sold in Italy by Laboratori Vaj S.p.A. The adhesives for topical attachment mentioned in WO 95/16424 include also today's pressure sensitive adhesives which are used to attach sanitary napkins to undergarments. Further, this document only identifies static rheological characteristics but is silent as to the dynamic rheological behaviour of a topical adhesive.

In WO 96/13238 a frequency dependent topical adhesive model is disclosed. However, all measurements disclosed, e.g. on page 9, were made at temperatures between −60° C. and +120° C. and at actual frequencies of 0.1 to 100 rad/s. In order to obtain the necessary data at application temperature (about 20° C., typical bath room, i.e. storage temperature) the Williams-Landel-Ferry (hereinafter WLF) equation was used.

This WLF equation is empirical and only valid within certain limits e.g. it cannot be used to extrapolate to temperatures below the glass transition temperature of a polymeric adhesive also the WLF cannot be used on the basis of values obtained below the glass transition temperature. Details about the WLF equation and its applicability can be found in "Principles of Polymer processing" by Z. Tadmor and C. G. Gogos, published by John Wiley & Sons or in "Viscoelastic Properties of Polymers" by J. D. Ferry also published by John Wiley & Son. Since this is already missing from WO 96/13238 the applicability of the disclosed data cannot be assessed.

European Patent Application EP-638 303 discloses the use of a topical adhesive on side cuffs of sanitary napkins in order to keep the cuffs in an upright position. Swiss publication CH-643730 discloses the use of a very long sanitary napkin having chamfered outer edges with a topical adhesive at the four corners of the outer edges in order to provide a topical adhesive area well outside the region of pubic hair growth. Both applications are silent as to the adhesive composition.

Based on the above state of the art it is an objective of the present invention to provide a topical adhesive for secure attachment and painless removal from the skin for articles outside the absorbent article field and/or for functional articles. It is another objective of the present invention to ensure upon removal that no residual adhesive remains on the skin or on the hair.

It is yet a further objective of the present invention that the adhesive for topical attachment does not cause a cold or otherwise unacceptable temperature sensation upon application despite a temperature difference of the adhesive in respect to the skin temperature.

In addition to the above objectives of the present invention it is also desirable for topical adhesives to provide additional benefits such as delivery/dispersal of a compound or composition which is beneficial for the skin or for the body in general. Further, topical adhesives which do not affect the natural skin condition, e.g. by being breathable or water vapour transmitting, are preferred.

BRIEF DESCRIPTION OF THE INVENTION

The present invention is useful to attach to the skin or wear protective articles such as genital-, knee- or elbow-protectors or bandages; clothing such as bras, surgical gowns, or parts of garments during fitting at a tailor; nasal plasters; prosthesis such as breast replacements or wigs; heat wraps, pads, and/or packs, e.g. for topical relief of pain or simply to provide warmth; cold wraps e.g. to provide pain relieve from bruises and to reduce swelling; hearing aids; protective face masks; ornamental articles such as jewelry, earrings, guises, tattoos; goggles or other eye wear. Such articles are non-absorbent for bodily liquids.

The present invention is also useful to attach functional articles to the skin or improve the function of such articles when worn on the skin. Functional articles are cosmetic or pharmaceutical delivery articles which provide a substance to the skin such as skin treatment substances, creams, lotions, hormones, vitamins, deodorants, or drugs; alternatively cosmetic or pharmaceutical delivery articles can also provide a substance to emanate away from the skin such as insecticides, inhalation drugs, or perfumes; further the adhesive of the present invention can also be used in functional articles which are not attached to the skin but as a component in articles which require a high residence time on the skin such as decorative cosmetics (lipstick, eye colors, stage make-up) or cleaning article (hand cleaner, face mask, hygienic cleanser especially for pores). Such articles also are non-absorbent for bodily liquids. The topical adhesive allows secure attachment of an article to the skin of the wearer and supports the functionality of the articles. The term "functional" in this context means that the article after being placed on the skin fulfills an additional function which is supported or improved by the topical adhesives according to the present invention.

The articles typically have a wearer or body facing surface and an outside surface. The topical adhesive allows to attach an article to the skin of the wearer, being provided as a layer having a certain thickness or caliper C measured in millimetres (mm).

Detailed analysis of the sequence of common situations occurring from the application of such articles to the time of removal has shown that specific adhesive characteristics need to be preferably satisfied in order to achieve the desired performance objectives, in particular secure initial attachment, secure attachment during use and painless removal at the end. The characteristics which have been considered in this context are the elastic modulus describing the elastic behaviour of the material and the viscous modulus which describes the viscous behaviour of the adhesive material.

The viscous behaviour of the adhesive can be interpreted to represent an indication of the ability of the adhesive to quickly attach and securely adhere. The elastic behaviour can be interpreted as an indication of the "hardness" behaviour of the adhesive. Its value is also critical for good initial attachment. Their combination is believed to be an indicator of the required force upon removal. The relation between elastic and viscous modulus is considered to be an indication on which fraction of the removal energy will be dissipated within the adhesive and which fraction is available to trigger the actual removal.

In order to provide topical adhesives for secure initial and prolonged attachment and easy/painless removal the relation between the elastic modulus and the viscous modulus as well as their dynamic behaviour is of key importance.

The topical adhesive has an elastic modulus at a temperature of 37° C. (100° Fahrenheit) abbreviated $G'_{37}$, a viscous modulus at a temperature of 37° C. (100° Fahrenheit) of $G''_{37}$, and a viscous modulus at a temperature of 25° C. (77° Fahrenheit) of $G''_{25}$. The adhesive further has a dynamic elastic behaviour defined as $\Delta G'_{37}$ which is the difference of $G'_{37}$ at a frequency of 100 rad/sec and $G'_{37}$ at a frequency of 1 rad/sec and a dynamic viscous behaviour $\Delta G''_{37}$ which is the difference of $G''_{37}$ at a frequency of 100 rad/sec and $G''_{37}$ at a frequency of 1 rad/sec.

The topical adhesive according to the present invention preferably satisfies the following conditions.

- $G'_{37}$ (1 rad/sec) is in the range 1500 Pa to 20000 Pa, preferably 1500 Pa to 15000 Pa, most preferably 3000 Pa to 10000 Pa.
- $G''_{37}$ (1 rad/sec) is in the range 100 Pa to 15000 Pa, preferably 100 Pa to 10000 Pa, most preferably 300 Pa to 5000 Pa.
- the ratio of $G'_{37}$ (1 rad/sec) / $G''_{37}$ (1 rad/sec) is in the range of 3 to 30.
- the ratio $$\frac{G'_{37} (100 \text{ rad/sec}) - G''_{37} (100 \text{ rad/sec})}{G'_{37} (1 \text{ rad/sec}) - G''_{37} (1 \text{ rad/sec})}$$

is not less than 0.5, preferably in the range 0.7 to 3, most preferably in the range 1 to 1.8.
- either the ratio of $\Delta G''_{37}/\Delta G'_{37}$ (1 rad/sec) is not greater than 1.5, preferably not greater than unity and most preferably not greater than 0.8, or $\Delta G'_{37}$ is not greater than 10000 Pa, preferably less than 5000 Pa, most preferably less than 2000 Pa, or both.

the value of the ratio $G'_{37}/G''_{37}$ at least for the frequency range from above 1 rad/s up to 100 rad/s should preferably be 3.3 or above, more preferably 5 or above, most preferably 10 or above, while not exceeding about 30, preferably 20, anywhere in the frequency interval.

the rheological behaviour can also be related to the values of the Glass Transition Temperature Tg. For topical adhesives according to the present invention Tg should preferably be less than $-15°$ C., more preferably less than $-20°$ C. and most preferably less than $-25°$ C.

the rheological behaviour and acceptance of a topical adhesive can also be related to the specific heat capacity. Preferably the specific heat capacity of the topical adhesive is less than 4 J/g/K, more preferably less than 3 J/g/K and most preferably less than 2 J/g/K.

the rheological behaviour and acceptance of a topical adhesive can also be related to the specific heat conductivity of the adhesive. Preferably the specific heat conductivity is as low as possible, preferably between 1 and 0.1 W/m/K, most preferably between 0.6 and 0.1 W/m/K . However, even though these ranges allow selection of appropriate adhesives, in the case of heat or cold wraps it is desirable to have a relatively high value of heat conductivity to support the function of such articles.

Provided the above rheological conditions are satisfied the adhesives will also satisfy conditions such as sufficient cohesiveness (to prevent residue of adhesive on skin) which are critical for commercial use of such adhesives and apparent to those skilled in the art. Adhesive compositions which satisfy the above criteria can be used as topical adhesives for the above mentioned articles provided they also satisfy the common requirements of being safe for use on human or animal skin during use and generally after disposal of the article.

Often the criteria of hygienic appearance and pleasant feel upon contact are important such that adhesive composition which are transparent or white, and which prevent a cold, unpleasant feeling upon application are preferred.

The above rheological criteria and other considerations can be satisfied by adhesive compositions where the composition comprises from 45%, preferably from 51%, to 99.5% of a plasticising compound or composition which is liquid at 20° C., from 0.5 to 20%, preferably 5% to 15%, of a polymeric compound or composition which is soluble or swellable in the plasticising compound or composition and with a tackifying resin in an amount in the range from 0% to 50% by weight of the composition, preferably from 0% to 600% by weight of the polymeric compound. The plasticising compound or composition is preferably selected from the group consisting of water, alcohols (preferably glycerol), glycols, polyglycols, liquid polybutenes, oil or combinations thereof. The polymeric compound or composition is preferably selected from the group consisting of block-copolymer-thermoplastic-elastomers, styrene-block-copolymers and hydrogenated styrene-block-copolymers, polyacrylics, polyvinyl alcohol, natural gum or gelatines, polyethyleneoxide, polyvinylpyrrolidon (PVP), polyvinylethers, cellulose derivatives, or combinations thereof.

According to the present invention, it has been discovered that the relation between the thickness or caliper C, measured in millimetres (mm), of the layer in which the topical adhesive is provided, e.g. onto at least part of the wearer facing surface of the article, and the viscous modulus $G''_{25}$ at about 100 rad/sec of the topical adhesive is relevant to the scope of providing an easy and painless removal from the wearer's skin of such a topical adhesive applied on at least part of the wearer facing surface of an article for attachment of said article to the skin of a wearer.

The topical adhesive of the present invention provided as a layer having a thickness C is such that the viscous modulus $G''_{25}$ (100 rad/sec) and the thickness C satisfy the following empirical equation:

$$G''_{25} \leq [(4.26+C) \cdot 1605] Pa$$

and preferably the following empirical equation:

$$G''_{25} \leq [(1.53+C) \cdot 1724] Pa$$

DETAILED DESCRIPTION OF THE INVENTION

Adhesive for topical attachment

The topical adhesive according to the present invention is applied directly to the skin. In a particular application the adhesive can be used on protective articles such as genital-, knee- or elbow-protectors or bandages; clothing such as bras, surgical gowns, or parts of garments during fitting at a tailor; nasal plasters; prosthesis such as breast replacements or wigs; heat wraps, pads, and/or packs, e.g. for topical relief of pain or simply to provide warmth; cold wraps e.g. to provide pain relieve from bruises and to reduce swelling; hearing aids; protective face masks; ornamental articles such as jewelry, earrings, guises, tattoos; goggles or other eye wear.

The topical adhesive according to the present invention can be also used in the context of functional articles such as cosmetic or pharmaceutical delivery articles which provide a substance to the skin such as skin treatment, substances, creams, lotions, hormones, vitamins, deodorants, or drugs; alternatively cosmetic or pharmaceutical delivery articles can also provide a substance to emanate away from the skin such as insecticides, inhalation drugs, or perfumes; further the adhesive of the present invention can also be used in functional articles which are not attached to the skin but as a component in articles which require a high residence time on the skin such as decorative cosmetics (lipstick, eye colors, stage make-up) or cleaning article (hand cleaner, face mask, hygienic cleanser especially for pores).

The word "skin" according to the present invention does relate to the outer surface of the derma of humans or animals.

In order to provide fixation of an article according to the present invention to the skin it is generally necessary to provide a certain area on the side of the article which is facing the skin with the topical adhesive.

The topical adhesive is provided with the preferred pattern, typically on the wearer facing surface of the article, as a layer having a thickness or caliper C that is preferably constant. The layer can be preferably continuous or alternatively discontinuous, e.g. in form of dots, spirals, or stripes.

Physical, Rheological and Adhesive Characteristics of a Topical Adhesive

Even though topical adhesives are used like pressure sensitive adhesives on human skin hair and mucous tissues, it is understood that the topical adhesive compositions could only with difficulty be considered typical pressure sensitive adhesives (referred to as PSA hereinafter) on the basis of the most characteristic rheological behaviours identifying such materials.

In fact as the person skilled in the art of adhesives knows, the most characteristic feature that distinguishes a PSA from other substances that can temporarily stick things (as e.g. water between two glass plates could) is the fact that their rheological parameters and especially the Elastic Modulus G' vary greatly with the frequency of applied stresses. More in particular, G' of PSA can increase over some orders of magnitude while the frequency of applied stresses varies from typical bonding frequency to typical debonding frequency, i.e. 1 rad/s to 100 rad/s as indicated below.

As a first consequence, it derives that it is inadmissible to define materials intended for use as "topical adhesives" by giving values of rheological parameters and especially of G' at a fixed value of frequency. This can be misleading because in the absence of other characteristics it will include materials which have no practical value. It is hence necessary that rheological characterisation must be on the base of dynamic considerations.

This not only applies to the Elastic Modulus G' but also to the viscous modulus G" and hence also for tan $(\delta)$=G"/G'. It is well known that typical PSA have not only a high variation of G' across the considered frequencies but also there is an even higher variation of G" which can get close or become even higher than the value of G', i.e. tan $(\delta)$ becomes about or even greater than 1, in particular at the frequencies that are typical of the debonding.

Without wishing to be bound by theory this can be interpreted as meaning that a high fraction of the energy applied for the debonding is dissipated within the adhesive (so it is not effective in causing the debonding) while this fact causes macroscopically the recording of a very high level of adhesive force.

As indicated above materials useful as topical adhesives according to the present invention have rheological characteristics which are mostly measured at a reference temperature of 37° C. (as usual body temperature of humans) and in a range of frequencies. It has been found that upon application of an article such as a wig or a vitamin plaster with a topical adhesive the adhesive contact is formed at a low frequency, while debonding happens at the speed of removing the article. This speed is expressed as a frequency of 100 rad/s while the low frequency of forming the adhesive bond has been found to be on the order of 1 rad/s. Therefore, the frequency range for use according to the present invention is between 1 and 100 rad/s.

It is believed that the adhesive bonding characteristics are selected most appropriately at human body temperature. Since the topical adhesive according to the present invention is used directly on skin and the person skilled in the art is directed to select the adhesive composition to have a small specific heat capacity (e.g. preferably less than 4 J/g/K) the actual temperature of the topical adhesive will reach 37° C. very quickly or even be warmed up by a human prior to application.

In order to provide good conditions of bonding, i.e. at a frequency of about 1 rad/sec, the absolute values of the elastic modulus should not be too high, otherwise the adhesive is too hard and it is not able to intimately join or mold to the surface to which it is expected to adhere. It is also important to have a low absolute value of G" in order to have good cohesion which is particularly valuable when using articles which are frequently removed and adhered again or replaced while the material remains soft and capable of gently adhering to skin.

The ratio of G'$_{37}$ (1 rad/sec) over G"$_{37}$ (1 rad/sec) is important to ensure that these two values are balanced upon adhesion to the skin. At the same time the absolute changes of G'$_{37}$ need to be limited within the range of frequencies considered. Hence a value for the ratio of $\Delta$G'$_{37}$ (i.e. G'$_{37}$ (100 rad/sec)−G'$_{37}$ (1 rad/sec)) over G'$_{37}$ (1 rad/sec) has to be kept small in order to maintain the secure attachment of the topical adhesive without causing discomfort over time or at removal/delamination. This can also be expressed in absolute terms by keeping the $\Delta$G'$_{37}$ below certain values.

Importantly, the ratio of $$\frac{G'_{37}(100\ \text{rad}/\text{sec}) - G''_{37}(100\ \text{rad}/\text{sec})}{G'_{37}(1\ \text{rad}/\text{sec}) - G''_{37}(1\ \text{rad}/\text{sec})}$$

needs to be large enough to ensure that the dynamic behaviour of both the elastic and the viscous module are maintained in a relationship which provides secure adhesion and painless and easy removal.

Finally the person skilled in the art will also recognise that the Glass Transition Temperature Tg of the adhesive composition, specific heat capacity, and specific heat conductivity are parameters which are useful to more fully define the group of useful topical adhesives.

The following set of characteristics should preferably be satisfied for the topical adhesive of the present invention:

- G'$_{37}$ (1 rad/sec) is in the range 1500 Pa to 20000 Pa, preferably 1500 Pa to 15000 Pa, most preferably 3000 Pa to 10000 Pa.
- G"$_{37}$ (1 rad/sec) is in the range 100 Pa to 15000 Pa, preferably 100 Pa to 10000 Pa, most preferably 300 Pa to 5000 Pa.
- the ratio of G'$_{37}$ (1 rad/sec) / G"$_{37}$ (1 rad/sec) is in the range of 3 to 30.
- the ratio $\frac{G'_{37}(100\ \text{rad/sec}) - G''_{37}(100\ \text{rad/sec})}{G'_{37}(1\ \text{rad/sec}) - G''_{37}(1\ \text{rad/sec})}$ is not less than 0.5, preferably in the range 0.7 to 3, most preferably in the range 1 to 1.8.
- either the ratio of $\Delta$G'$_{37}$/G'$_{37}$ (1 rad/sec) is not greater than 1.5, preferably not greater than unity and most preferably not greater than 0.8, or $\Delta$G'$_{37}$ is not greater than 10000 Pa, preferably less than 5000 Pa, most preferably less than 2000 Pa, or both.

the value of the ratio G'$_{37}$/G"$_{37}$ at least for the frequency range from above 1 rad/s up to 100 rad/s should preferably be 3.3 or above, more preferably 5 or above, most preferably 10 or above, while not exceeding about 30, preferably 20, anywhere in the frequency interval.

the rheological behaviour can also be related to the values of the Glass Transition Temperature Tg. For topical adhesives according to the present invention Tg should preferably be less than −15° C., more preferably less than −20° C. and most preferably less than −25° C.

the rheological behaviour and acceptance of a topical adhesive can also be related to the specific heat capacity. Preferably the specific heat capacity of the topical adhesive is less than 4 J/g/K, more preferably less than 3 J/g/K and most preferably less than 2 J/g/K.

the rheological behaviour and acceptance of a topical adhesive can also be related to the specific heat conductivity of the adhesive. Preferably the specific heat conductivity is as low as possible (except for energy transmitting articles where high values are more desirable), more preferable between 1 and 0.1 W/m/K, most preferably between 0.6 and 0.1 W/m/K.

Chemical and compositional characteristics of a Topical adhesive

In order to provide topical adhesive compositions which satisfy the requirements of the above rheological and physical characteristics of a topical adhesive the following formulation criteria can be used in addition. It should be noted that the most of the compositions useful as topical adhesive have a substantially gel-like structure and are preferably gels. This derives from the fact that:

the prevailing component is the plasticiser which is a material liquid at room temperature a macromolecular or polymeric component is present in minor quantities vs. the plasticiser. It forms, in the preferred embodiments, a three dimensional network caused by physical or chemical links between the molecules. Particularly useful physical links are the ones present in systems containing Block Thermoplastic Elastomers.

More specifically, the compositions typically comprise:

from 0.5 to 20%, preferably 5% to 15%, by weight of a macromolecular polymeric substance or a mixture of such substances soluble or swellable in the below mentioned plasticiser(s). As not limiting examples such macromolecular or polymeric substances can be natural and/or synthetic such as natural gums or derivatives such as natural gums and gelatins, their derivatives and alginates; polyacrilics, polyvinyl alcohol; polyethylene oxide; polyvinylpyrrolidon (PVP) or polyvinylethers, their copolymers and derivatives; cellulose derivatives; Block Copolymer Thermoplastic Elastomers and preferably Styrenic Block Copolymers and more preferably the hydrogenated grades Styrol/Ethylene-Butylene/Styrol (SEBS), Styrene/Isoprene/Styrene (SIS), and Styrol/Ethylene-Propylene/Styrol (SEPS).

from 45 to 99.5% by weight, preferably from 51 to 99.5% by weight, of a plasticising substance or a mixture of plasticising substances, which are liquid at room temperature. As non-limiting examples the plasticiser can be water, various alcohols (like in particular glycerol), glycols and their ethers, polyglycols, liquid polybutenes, esters such phthalates, adipates, stearates, palmitates, sebacates, or myristates, natural or synthetic oils such as vegetable oils, mineral oils, or combinations thereof.

from 0% to 50% by weight of the composition, preferably from 0 to 600% by weight of the macromolecular polymeric substance of a tackifying resin whose main scope is to tailor the Tg especially in systems based on synthetic polymers.

from 0 to 10% and more preferably form 0 to 5% by weight of substances for facilitating and stabilising the gel and the gel forming process both of hydrophilic or hydrophobic liquid plasticisers. These may be for oily systems, e.g. the fatty acids of $C_8$ to $C_{22}$, their metallic salts and their polyoxo-derivatives; lanolin derivatives; silica; bentonite, montmorillonite and their derivatives; polyamides, waxes or mixtures thereof.

Common additives known in the art as preservatives, antioxidants, anti UV, pigments, mineral fillers, rheology modifiers etc. can also be comprised in quantities up to 10% each.

When chemical crosslinks are formed in the system, a crosslinking agent can be present preferably in quantities up to 5% by weight. Chemical crosslinking can be formed also by mutual neutralisation of polymers having different functionalities as in the reaction between acid polyacrylics and polysaccharides.

The resulting compositions for topical adhesives can be divided into three families according to the nature of the main component, i.e. usually the liquid plasticiser(s):

1) Hydrophobic compositions in which the plasticiser is typically an oil or blend of oils of vegetable or mineral origin and the polymer is usually a synthetic polymer, preferably an elastomer, soluble or swellable in oil(s).

2) Mixed phase compositions in which both hydrophobic and hydrophilic components, possibly in both plasticisers and polymers, form two or more separate phases. In such cases an emulsifier/surfactant is preferably present at a suitable level to form stable emulsions between the incompatible phases. For topical adhesives according to the present invention it is preferably that the hydrophobic components are prevailing vs. the hydrophilic ones.

3) Hydrophilic compositions in which typically the plasticiser is water/glycerol/glycols and the like and/or mixtures thereof and the polymeric phase is of synthetic (e.g. polyacrilics) or natural (e.g. natural gums) origin or mixtures thereof.

It is to stress that, differently from the medical field and from the cited prior art, the hydrophilic compositions are not preferred while the hydrophobic and mixed phases compositions 1) and 2) are preferred in the applications of the present invention.

This depends partially on technical reasons in the sense that many hydrophilic compositions used in the medical field show too low elastic character and cohesion for being useful in the present application.

For example, for most functional articles mixed phases compositions are preferred. For functional articles with a delivery function the compound to be delivered needs to come out of the topical adhesive composition at different speeds, e.g. perfumes can have a delivery profile which changes from high to lower values while drugs have to be delivered preferably at a constant rate to prevent overdosing. Cosmetics often are lipophilic and moisturizing such that a combination of watery and oily components is most desirable.

Further hydrophilic topical adhesives also tend to be perceived as cold and wet which upon application to the skin of a human is not in line with typical expectation. Additional problems result from the fact that in particular topical adhesives comprising water as the plasticiser have a tendency to dry out unless they are sealed into an impermeable package.

Application of topical adhesive

Articles, comprising functional articles as previously defined, in which the topical adhesive according to the present invention can be used by being provided as a layer having a thickness or caliper C measured in millimetres (mm), can be made by any of the ways usual in the art. The functional article in this context also defines whether the adhesive is provided to hold a substrate to the skin or whether the adhesive as part of a composition is directly provided to the skin. In the first case the application of the adhesive to the skin facing surface of such articles should not cause major problems to those skilled in the art since it can be provided by any well known techniques commonly used for other adhesives. In this context the total area of the skin or wearer facing surface of an article which is covered by the topical adhesive depends on the intended use of the article. For conservation of adhesive it should be not more than 80%, preferably from 30% to 60% of the wearer facing surface of the article. Preferably, the adhesive extends close to the periphery of the article, but since it is not intended for absorbent articles it can also cover the central area of the articles. Most preferably the topical adhesive is provided in a pattern of small incremental areas such as dots or similar.

The topical adhesive is provided, e.g. on at least part of the wearer facing surface of the article, as a layer having a thickness or caliper C that is preferably constant, or that alternatively can vary over the surface interested by the application of the topical adhesive.

If possible, the article also provides breathability by being at least water vapour permeable, preferably air permeable to prevent stuffiness. Breathability, if not supported by the topical adhesive as such, can be limited to the area of the article where no adhesive is applied.

The topical adhesive on an article is preferably protected prior to use. This protection can be provided by a release liner such as a siliconised or surfactant treated paper, providing easy release for the selected topical adhesive.

When considering particularly the removal phase of a topical adhesive composition for attachment of articles to the skin of a wearer, it is commonly recognized that good conditions of removal, i.e. at a frequency of about 100 rad/sec, of the topical adhesive applied to at least part of the wearer facing surface of an article for attachment of said article to the skin of a wearer, are achieved when the adhesive can be easily removed from the skin, and particularly from the hairs that can possibly be present on it where the article contacts the body, without causing pain to the wearer, therefore without sticking too hard upon removal to the skin and hairs of the wearer. Moreover, a good removal implies that the topical adhesive does not leave residual remains on the skin or on the hairs.

According to the present invention, the relationship between the thickness or caliper C measured in millimetres (mm) of the layer in which the topical adhesive is provided, e.g. typically onto at least part of the wearer's facing surface of the article, and the viscous modulus $G''_{25}$ at 25° C. and at about 100 rad/sec of the topical adhesive gives an indication on the painless and easy removal of the topical adhesive from the skin.

Without being bound to any theory, it is believed that for higher values of $G''_{25}$ at 100 rad/sec, which overall correspond to a higher adhesiveness of the composition, a thicker caliper or thickness C of the adhesive layer is needed so that the energy applied for the removal is more evenly distributed within the mass of the adhesive, and is therefore transferred smoothly to the skin, so avoiding peaks of energy that typically cause the pain sensation to the wearer. In other words, thinner layers of the topical adhesive necessitate an adhesive with a lower $G''_{25}$ at 100 rad/sec to achieve a reduced pain sensation upon removal of the article.

According to the present invention, the topical adhesive of the present invention provided as a layer having a thickness C measured in millimetres (mm), is such that the viscous modulus $G''_{25}$ (100 rad/sec) and the thickness C of the adhesive layer satisfy the following empirical equation:

$$G''_{25} \leq [(4.26+C) \cdot 1605] Pa$$

and preferably the following empirical equation:

$$G''_{25} \leq [(1.53+C) \cdot 1724] Pa$$

While in a preferred embodiment of the present invention the thickness C of the adhesive layer is constant, such adhesive layer can also have different thicknesses in different portions of the wearer facing surface of the article where it is applied, provided that the above mentioned relationship between C and $G''_{25}$ is in any case satisfied.

In order to evaluate the effect of the thickness C of the topical adhesive layer in its relationship with the viscous modulus $G''_{25}$ (100 rad/sec) of the topical adhesive of the present invention on the removal of the topical adhesive used for the attachment of an article to the skin of a wearer, a Removal Pain Grade Test has been developed. In this test the adhesion of standard substrates, on which the same topical adhesive has been provided in layers having different thicknesses, on the skin of the forearm of members of a sensory panel is achieved, and upon successive removal the pain is evaluated in terms of pain grade.

Removal Pain Grade Test

The Removal Pain Grade Test is utilized to evaluate the pain during removal from the skin of a wearer of a sample provided with a layer of a topical adhesive and previously attached to the wearer's skin. The test specifically evaluates the pain upon removal of each sample as compared to the pain obtained by removing a reference sample constituted by a commercial strong medical plaster.

Sample Preparation.

The test is performed on rectangular samples 60×20 mm made of a polyester film 23 μm thick, such as that sold by Effegidi S.p.A. of Colorno (Parma, Italy), provided on one side with a continuous layer of the topical adhesive having the selected thickness, applied with an Acumeter Model LH-1 extruder. The reference sample is a 60×20 mm sample of a medical double sided adhesive tape produced by Minnesota Mining and Manufacturing Company under the trade name of No. 1524 Medical Tape; only one of the two layers of adhesive is exposed on the reference sample and used for attachment to the skin during the test.

Test Method.

A panel of six graders is selected for the test. The test is performed in a climatically controlled lab where a temperature of 23° C. and a Relative Humidity of 50% are maintained. No special treatment of the wearer's skin is required beyond normal cleaning/washing with water and soap and drying at least two hours before the test to allow equilibrium with the room conditions is reached for the skin. Three different samples A, B, and C are evaluated in the test in comparison with the reference sample R. Each sample is applied by hand by an operator to the inner part of the grader's forearm, being centered between the wrist and the elbow, with the short side of the sample aligned with the length of the arm. The operator exerts on each sample with his palm the same pressure that is typically applied to cause a medical plaster to adhere to the skin. Each sample is worn for the prescribed time, and then it is removed from the grader's skin by the operator with a slow and smooth pull.

Four series of one reference sample R and three samples A, B, and C each are applied, worn and then removed from the wearer's skin; each sample is worn for one minute, with a 5 minute wait between two subsequent samples of the same series, and a 15 minute wait between two different subsequent series. The reference sample R is always applied, worn and removed as the first sample of its respective series. The sequence of application/wear/removal of A, B, C samples in each of the first three series is random, provided that no repetition in each series is allowed, and that no sequence is repeated in the first three series. In the fourth series of four samples one of A, B, or C samples is tested twice, the reference R always being the first one.

Overall each sample (A, B, C, and R) has to be tested an equal number of times (24 times according to the scheme below).

In the performed tests the sequences of the four series are according to the following scheme:

| Grader | 1st series | 2nd series | 3rd series | 4th series |
|--------|-----------|-----------|-----------|-----------|
| 1 | RABC | RCAB | RBCA | RAAB |
| 2 | RCAB | RBCA | RABC | RBCC |
| 3 | RBCA | RABC | RCAB | RCAA |
| 4 | RABC | RCAB | RBCA | RBBC |
| 5 | RCAB | RBCA | RABC | RAAB |
| 6 | RBCA | RABC | RCAB | RBCC |

The graders were asked to evaluate each sample A, B and C using a pain scale ranging from 0 to 10, where 0 corresponds to no pain and 10 corresponds to the pain upon removal of the reference sample R.

The pain values for each sample A, B, and C were obtained as a mean of 24 observations.

The results collected from the test were analyzed by a statistical analysis program "Comparison of Population Means—Paired Samples", that showed that the differences between the pain values of the samples A, B, and C are statistically significant.

The pain upon removal was evaluated according to the Removal Pain Test for three different samples A, B, and C, each constituted by the same standard substrate on which the same topical adhesive composition is provided as a uniform layer of predetermined thickness.

The topical adhesive is an oil based composition containing 10% by weight of Kraton G-1651, a Styrene/Ethylene-Butylene/Styrene block copolymer available from Shell Co., 49% by weight of Kaydol, a paraffinic mineral oil available from Witco Co., 40% by weight of Escorez 5300, a hydrogenated tackifying resin available from Exxon Co., 0.7% by weight of Magnesium Stearate, a co-gelifying agent for oil available from Carlo Erba S.p.A., and 0.3% by weight of Irganox 1010, an antioxidant available from Ciba-Geigy.

So finally the formulation had the following percent composition:

| Kraton G-1651 | 10.0% by weight |
| Kaydol | 49.0% by weight |
| Escorez 5300 | 40.0% by weight |
| Magnesium Stearate | 0.7% by weight |
| Irganox 1010 | 0.3% by weight |

The composition has the following rheological properties at 37° C.

a) Elastic Modulus at 1 rad/s, $G'_{37}$=7038 Pa b) Viscous Modulus at 1 rad/s, $G''_{37}$=487 Pa c) Ratio of Elastic and Viscous Modulus at 1 rad/s, $G'_{37}/G''_{37}$=14.45 d) Ratio of $$\frac{G'_{37}(100 \text{ rad/sec}) - G''_{37}(100 \text{ rad/sec})}{G'_{37}(1 \text{ rad/sec}) - G''_{37}(1 \text{ rad/sec})} = 1.11$$

e) The ratio of $\Delta G'_{37}$ over $G'_{37}$ (1 rad/s) was 0.291, with $\Delta G'_{37}$=2051 Pa.

The composition further has a viscous modulus $G''_{25}$ at 25° C. and at about 100 rad/sec of 4431 Pa.

The thickness of the adhesive layers of the three samples and the respective pain grades are shown in the following table:

| Substrate | Thickness (mm) | Pain grade |
|-----------|---------------|-----------|
| A | 1.800 | 3.79 |
| B | 0.555 | 5.67 |
| C | 0.140 | 7.33 |

The results show that for a given topical adhesive composition, represented by the value of $G''_{25}$ (100 rad/sec) of 4431 Pa, increasing thickness values for the layer of topical adhesive correspond to reduced pain grades upon removal of the topical adhesive from the skin Of course the thickness values for topical adhesive layers comprised in different articles can be varied according to the empirical equations of the present invention in order to achieve acceptable removal pain grades with different topical adhesive compositions, and therefore with different values of $G''_{25}$ (100 rad/sec), within limits that can be readily determined by the man skilled in the art. Usually, in the field of the articles previously defined, this limit should not exceed 10 mm. The same is true for possible selection of preferred topical adhesive compositions having different values of $G''_{25}$ (100 rad/sec) to be applied in a layer having a certain preferred thickness in order to reduce the pain grade upon removal of the article form the skin. Possible preferred limits for $G''_{25}$ (100 rad/sec) of a topical adhesive composition are implicitly defined e.g. by the preferred rheological characteristics of the topical adhesive compositions.

What is claimed is:

1. A combination of a substrate with a hydrophobic topical adhesive applied thereon, said adhesive comprising at least 80% by weight of hydrophobic components, said combination intended for attachment of a topical adhesive for attachment to the skin of articles such as protective articles, clothing, prosthesis, heat wraps, pads, and/or packs, cold wraps, hearing aids, protective face masks, ornamental articles or eye wear, or functional articles being cosmetics or cleaning articles, but excluding disposable absorbent articles such as wound dressing, sanitary napkins, pantiliners, incontinence articles or underarm sweat pads, said topical adhesive being provided as a layer having thickness C measured in millimeters (mm), said topical adhesive having an elastic modulus at a temperature of 37° C. (100° F.), G'37, in the range of 3000 Pa to 10000 Pa, a viscous modulus at a temperature of 37° C. (100° F.), G"37, in the range of 300 Pa to 5000 Pa, a viscous modulus at a temperature of 25° C. (77° F.), G"25, characterized in that said viscous modulus $G''_{25}$ (100 rad/sec) of said topical adhesive of said topical adhesive and said thickness C satisfy the following equation:

$$G''_{25} \leq [(4.26+C) \cdot 1605] Pa$$

and wherein the ratio $$\frac{G'37 \ (100 \ rad/sec) - G''37 \ (100 \ rad/sec)}{G''37 \ (1 \ rad/sec) - G''37 \ (1 \ rad/sec)}$$

is in the range 1 to 1.8.

2. A topical adhesive according to claim 1, wherein said viscous modulus $G''_{25}$ (100 rad/sec) and said thickness C satisfy the following equation:

$$G''_{25} \leq [(1.53+C) \cdot 1724] Pa.$$

3. A topical adhesive according to claim 1, wherein said adhesive is provided as a continuous layer.

4. A topical adhesive according to claim 1 comprising
   from 45% to 99.5% by weight of a plasticising compound or composition which is liquid at 20° C.;
   from 0.5% to 20% by weight of a polymeric compound or composition which is solvable or swellable in said plasticising compound or composition;
   a tackifying resin in an amount of from 0% to 50% by weight of said polymeric compound or composition.

5. A topical adhesive according to claim 1, wherein said articles are protective articles, clothing, prosthesis, heat wraps, pads, and/or packs, cold wraps, hearing aids, protective face masks, ornamental articles, eye wear or make-up, or on functional articles being cosmetic or pharmaceutical delivery articles, decorative cosmetics or cleaning articles.

6. A topical adhesive according to claim 1, wherein alternatively either
   $G'_{37}$ (100 rad/sec)–$G'_{37}$ (1 rad/sec) is not greater than 5000 Pa; or
   the ratio $$\frac{G'_{37} \ (100 \ rad/sec) - G'_{37} \ (1 \ rad/sec)}{G'_{37} \ (1 \ rad/sec)}$$

is not greater than 1.

7. A topical adhesive according to claim 1, wherein alternatively either
   $G'_{37}$ (100 rad/sec)–$G'_{37}$ (1 rad/sec) is not greater than 5000 Pa; or
   the ratio $$\frac{G'_{37} \ (100 \ rad/sec) - G'_{37} \ (1 \ rad/sec)}{G'_{37} \ (1 \ rad/sec)}$$

is not greater than 0.8.

8. A topical adhesive according to claim 1, wherein said adhesive is selected to have
   alternatively either
   $G'_{37}$ (100 rad/sec)–$G'_{37}$ (1 rad/sec) is not greater than 2000 Pa; or
   the ratio $$\frac{G'_{37} \ (100 \ rad/sec) - G'_{37} \ (1 \ rad/sec)}{G'_{37} \ (1 \ rad/sec)}$$

is not greater than 1.

9. A topical adhesive according to claim 1, wherein said adhesive is selected to have
   alternatively either
   $G'_{37}$ (100 rad/sec)–$G'_{37}$ (1 rad/sec) is not greater than 2000 Pa; or
   the ratio $$\frac{G'_{37} \ (100 \ rad/sec) - G'_{37} \ (1 \ rad/sec)}{G'_{37} \ (1 \ rad/sec)}$$

is not greater than 0.8.

\* \* \* \* \*